United States Patent [19]

Cannon

[11] Patent Number: 4,813,951
[45] Date of Patent: Mar. 21, 1989

[54] SELF-ACTUATED IMPLANTABLE PUMP

[75] Inventor: Robert L. Cannon, Conlie, France

[73] Assignee: Joel Wall, Hopkinton, Mass. ; a part interest

[21] Appl. No.: 52,471

[22] Filed: May 20, 1987

[51] Int. Cl.⁴ .............................................. A61M 5/00
[52] U.S. Cl. ................................. 604/891.1; 604/132; 604/185
[58] Field of Search ..................... 604/9, 93, 123, 132, 604/153, 175, 181, 183, 185, 186, 212, 217, 246, 890.1, 891.1; 128/DIG. 12

[56] References Cited

U.S. PATENT DOCUMENTS

| | | | |
|---|---|---|---|
| 4,193,397 | 3/1980 | Tucker et al. | 604/93 |
| 4,258,711 | 3/1981 | Tucker et al. | 604/93 |
| 4,329,985 | 5/1982 | Bonchek | 604/185 |
| 4,544,371 | 10/1985 | Dormandy, Jr. et al. | 604/891 |
| 4,588,394 | 5/1986 | Schulte et al. | 604/9 |
| 4,634,427 | 1/1987 | Hannula et al. | 604/93 |
| 4,710,167 | 12/1987 | Lazorthes | 604/93 |
| 4,718,894 | 1/1988 | Lazorthes | 604/93 |

FOREIGN PATENT DOCUMENTS 0177250 4/1986 European Pat. Off. ............ 604/246

OTHER PUBLICATIONS

Perry Blackshear, "Implantable Drug-Delivery Systems," *Scientific American*, Dec. 1979, pp. 66-74.

*Primary Examiner*—Stephen C. Pellegrino
*Assistant Examiner*—Ralph Lewis
*Attorney, Agent, or Firm*—Joel Wall

[57] ABSTRACT

An implantable pump, actuated by the patient in whom the pump is implanted, to provide pain relief and/or other therapeutic benefits. There is disclosed a fully implantable pump system, including a reservoir for holding fluid, a septum by which the reservoir is periodically refilled, and a resilient pump chamber responsive to manual pressure, for delivering limited amounts of the fluid through a catheter to a specific location within the body of the patient. Alternative embodiments disclosed include designs incorporating "windkessel-like" devices for controlling discharge of the fluid to the specific location to occur over extended time periods at relatively constant flow rates.

4 Claims, 4 Drawing Sheets

SELF-ACTUATED IMPLANTABLE PUMP

BACKGROUND OF THE INVENTION

1. Field of the Invention

This invention relates generally to that class of inventions which includes patient implantable prosthetic devices which offer therapeutic benefits to such patients. More specifically, this invention relates to an implantable, patient-actuated, pump.

2. Description of Prior Art

In the broad field of implantable prosthetic devices, one might encounter a wide spectrum of technology ranging from implantable demand heart pacemakers to implanted artificial hip sockets. However, the prior art for the present invention falls within a narrower category of technology relating to implantable pumps.

Companies are today offering implantable pumps in the market place. One particular company offers an expensive pump system that incorporates complicated mechanism: a pump motor, microelectronics, lithium batteries, external (hand-held) programming devices, etc. The programming devices incorporate radio-frequency transmission to control the pump. While this pump might be attractive as a research device, the cost and complexity of this pump preclude its general therapeutic use.

Another pump available to the marketplace today consists of two chambers separated by a flexible metal bellows: one chamber acts as a drug reservoir, while the other is the sealed power supply containing a two-phase charging fluid in equilibrium. Working with vapor pressures, condensations to the liquid state, etc., this system eliminated need for batteries. But, the fluid is again pumped to certain patient locations without any control by the patient and is inherently unresponsive to changing patient needs.

The kinds of therapeutic applications undertaken by these pumping schemes are many. They include application of nitroglycerine for coronary vascular spasm, application of theophyeline for asthma, application of antineoplastic agents (chemotherapy) for cancer, application of lidocaine for cardiac arrythmia, application of antimicrobial and antiviral agents for chronic infection (e.g. osteomyelitis), application of morphine and other opiates, endorphines, substance P for chronic intractable pain, and many other applications of other substances/drugs for other medical maladies. In many, if not all of these instances, an improvement would be achieved if the application were made when the patient sensed the need for the substance, and then controlled the application of the substance.

There is a large market for these pump devices. In the United States alone, with respect to the subject of cancer chemotherapy, there are 850,000 new cases per year; there are 1.8 million persons suffering chronic or intractable pain; and 0.5 million new cases per year needing chronic antibiotic therapy. All of these human beings would benefit from drug substances that could be pin-point applied to the area of need, and only when needed.

It is thus understood that there are shortcomings in the prior art: this therapy may be provided at varying rates, and programmable rates, but never in direct response to patient needs, as sensed by the patient. Applicant has seized upon a solution to this shortcoming, and to implantable pump shortcomings associated with complicated technology, and discloses and claims herein a significant advance in the art of implantable pumps.

SUMMARY OF THE INVENTION

There is provided a pump apparatus which is capable of being implanted within the body of a patient. The apparatus includes a reservoir for holding fluid to be pumped. The apparatus further includes a resilient pump chamber mechanism for withdrawing fluid from the reservoir and for supplying the fluid to a specific location within the body of the patient, but only when the patient manually applies force to the implanted resilient chamber.

Further features of the invention include windkessel devices for extending the flow of the fluid to the specific body location for longer durations at steady flow rates, which is desirable to combat certain medical infirmities.

It is thus advantageous to use the present invention in certain patients who can benefit from drug/substance therapy applied to specific locations under controlled conditions.

It is thus a general object of the present invention to provide an improved prosthetic device.

It is a more specific object of the present invention to provide an improved implantable pump for therapeutic purposes.

It is another object of the present invention to provide an improved, implantable pump, having the advantages of uncomplicated and reliable design in combination with self-actuation of the pump under control of the patient in whom such pump is implanted.

Other objects and advantages shall be understood from a reading of the Detailed Description of the Preferred Embodiments wherein:

DESCRIPTION OF THE PREFERRED EMBODIMENTS

Figure 1:
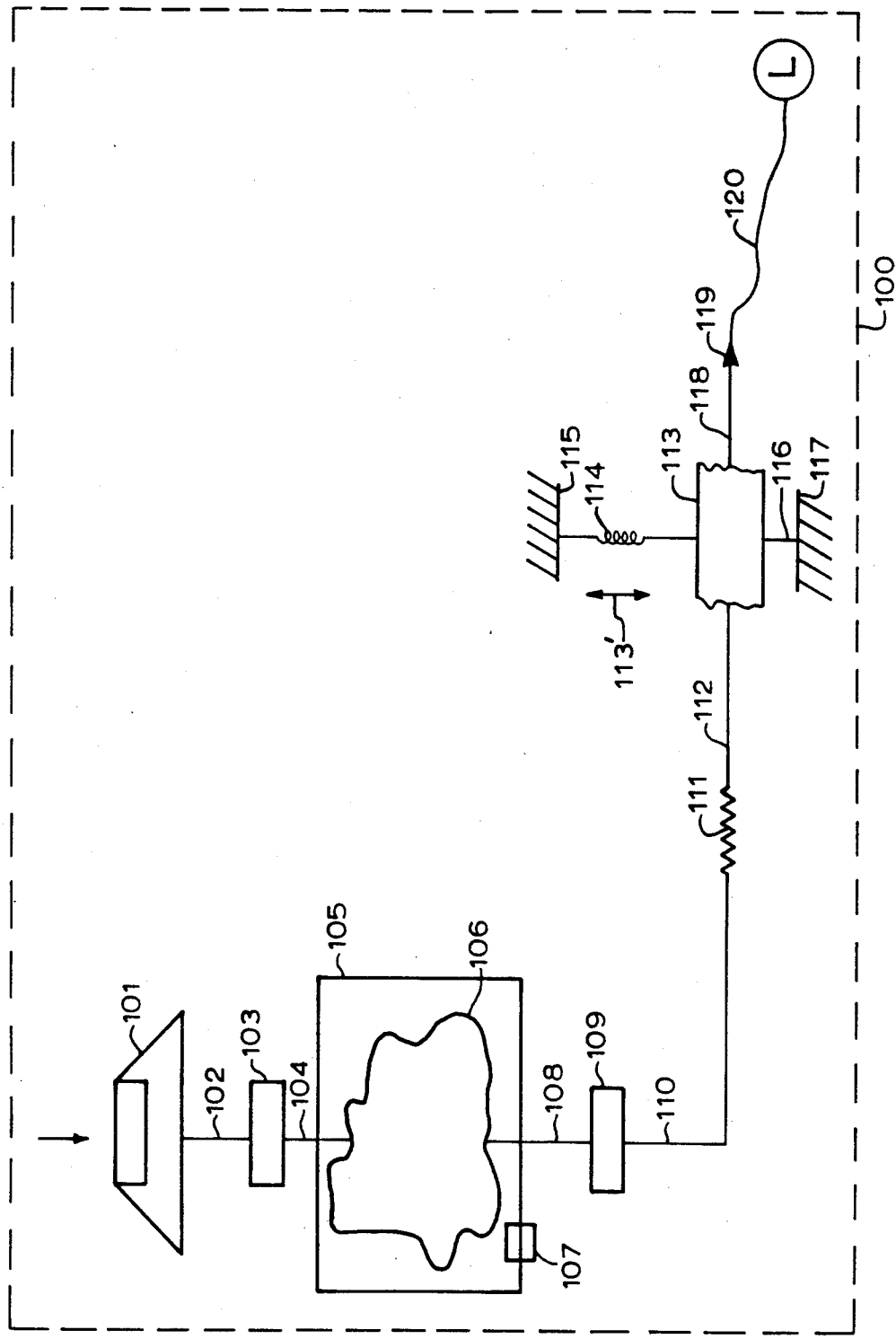
FIG. 1 is a schematic diagram of the preferred embodiment of the present invention.

Referring to FIG. 1, reference numeral 100 represents the (boundary of the) patient; thus all of the pump system is shown implanted within the patient's body. The pump system is shown in schematic format for ease of explanation of operation.

First, with respect to an interconnection description, septum 101 is connected via fluid conductor 102 through bacterial filter 103 and fluid conductor 104 to colapsible reservoir sac 106 positioned within rigid protective shield/enclosure 105. Bacterial filter 107 permits fluid flow between the patient and the enclosure shield 105 as sac 106 expands/collapses. Fluid from reservoir sac 106 is conducted via fluid conductor 108, bacterial filter 109, fluid conductor 110, fluid resistance 11, and fluid conductor 112 to resilient pump chamber 113. Resilient pump chamber 113 is adapted to be compressed in downward direction of arrow 113', its resilience represented by spring 114 connected between chamber 113 and fixed support 115; fixed support 116/117 is shown connected to the other side of pump chamber 113, the construction of which will be detailed later. The fluid output of pump chamber 113 is provided on fluid conductor 118, through one-way fluid valve 119, to catheter 120, to a particular location "L" within patient 100.

In operation, and continuing to refer to FIG. 1, the patient manually depresses resilient chamber 113, thereby forcing fluid therein into fluid conductor 118. Chamber fluid will not squirt back into fluid conductor 112, because of high resistance 111. This fluid flows through one-way valve 119 and through catheter 120 into the patient. The volume of fluid displaced is not greater than the volume of fluid in the chamber. The pump chamber has a preformed shape and a predetermined maximum chamber volume. The patient may prefer to not depress the chamber completely, and therefore less than the maximum volume of the fluid will be supplied to the patient.

When the patient removes the compressing force on chamber 113, its resilence causes it to return to its preformed shape as it sucks more fluid from reservoir sac 106, (and not from catheter 120 becuase of the orientation of one-way valve 119). However, fluid flow from reservoir sac 106 into pump chamber 113 is controlled by fluid resistance 111 to a predetermined refill rate, to prevent patient 100 from supplying fluid to specific patient locations at a rate faster than a predetermined acceptable supply rate. (Resistance 111 could be replaced with a one-way valve, with low-resistance direction oriented towards chamber 113, in those instances where maximum dosage rate is not an important issue.) After pump chamber 113 has been refilled, either fully or partially, pump chamber 113 can once again be depressed by the patient, to cause discharge of pump chamber fluid into the patient. This procedure can be repeated as long as fluid from reservoir sac 106 is sufficient to refill pump chamber 113.

If reservoir sac 106 is empty, and if chamber 113 is empty, then the pump system cannot provide additional fluid to the patient unless the reservoir is refilled. Refillng is accomplished by use of a self-sealing septum 101, designed to receive a needle through the skin surface of the patient thus establishing a temporary connection to a syringe. This refilling operation would typically be performed by a physician or other skilled medical practitioner. The fluid from the syringe thus passes through septum 101, fluid conductor 102, bacterial filter 103, fluid conductor 104, into reservoir sac 106. As sac 106 collapses, bacterial filter 107 passes lymph fluid from the patient into the rigid enclosure 105 to maintain pressure on the fluid in the sac relatively constant; and, as reservoir sac 106 is refilled, the lymph inside of enclosure 105 is forced out through bacterial filter 107 into the patient's body.

Rigid enclosure 105 is required to protect and make "puncture-proof" collapsible sac 106; if the needle from the refilling syringe were to puncture sac 106, the fluid leakage therefrom would be uncontrollable and could be harmful to the patient. (Although the pump chamber 113 is resilient, it must likewise be puncture-proof, accomplished by incorporating a titanium or molded-epoxy shield on the outer surface of the chamber.) Rigid enclosure 105 also serves as the fixed supports 115 and 117. Bacterial filters are required to keep bacterial levels to safe ranges, and, fluid resistance 111 consists of a long, thin tube, perhaps 150 microns inside diameter and three or four meters long, its resistance proportional to its length and inversely proportional to the fourth power of its inside diameter.

Figure 5:
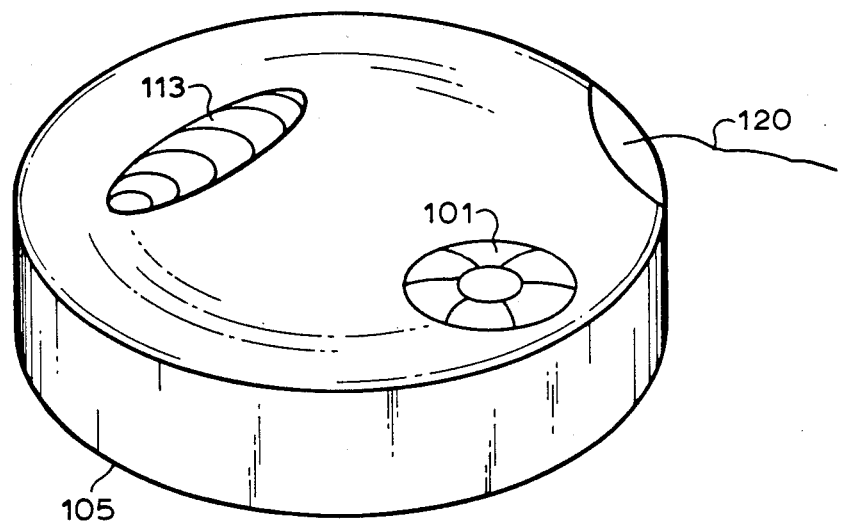
FIG. 5 is a perspective view of the implantable pump.

Referring to FIG. 5, the shell or enclosure 105 would typically be constructed from titanium or epoxy, and sac 106 (not visible on FIG. 5) would be constructed of silicone rubber or polyurethane. The outer dimensions of the shell would be about 50 millimeters diameter, by about 15 millimeters depth. The pump chamber 113 would be protruding above the surface of the enclosure to make it desirable for patient actuation; but the reservoir sac would be securely contained internally to the enclosure. Septum 101 is likewise protruding above the surface of container 105, easily accessed by a syringe needle. The maximum volume of typical pump chambers can be designed to range between 50 micro-liters and 250 micro-liters. The value of the resistance 111 is chosen to be that appropriate value to prevent refilling chamber 113 too rapidly under the medical circumstances in any particular instance.

Figure 2:
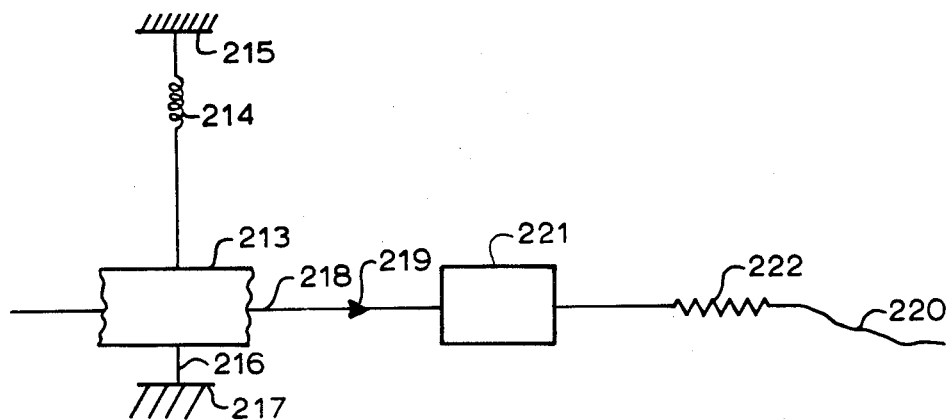
FIG. 2 is a schematic diagram of a first alternative embodiment of the present invention.

Referring next to FIG. 2, it is to be understood that the equivalent of the apparatus of FIG. 1 connected to the input to pump chamber 113, is assumed to be connected to the input to pump chamber 213, and is not shown for enhancement of clarity of presentation. Spring 214 and fixed supports 215 and 216/217 are equivalent to Spring 114 and fixed supports 115 and 116/117 respectively. Pump chamber 213, is resilient as expressed pictorially by spring 214, and moves in downward direction 213', responsive to manual force exerted by the patient. One way valve 219 permits fluid to flow only from chamber 213 via fluid conductor 218 into windkessel-device 221, and not in the reverse direction. The fluid output of windkessel 221 is conducted through fluid resistance 222 to catheter 220 and to a specific location within the patient. Windkessel 221 is a balloon-like mechanism, with resilience, such that the pressure it exerts is essentially independent of the volume it contains , which expands with in-flow of fluid from pump chamber 213, and which collapses slowly with out-flow of fluid through resistance 222. The value of resistance 222, and the elasticity of the windkessel, and other influences, control the out-flow rate. (The flow is to some extent dependent upon pressure in the windkessel, viscosity of the drug, size of the orifice, etc.) The effect of employing windkessel 221 is to provide a dosage of fluid to a specific location within the patient over a prolonged period of time, perhaps on the order of hours. This long lasting application of fluid may be particularly beneficial in certain chemo-therapy applications for cancer patients, or in other intractable pain situations where the anaesthetic is needed for longer durations.

In a particular embodiment, the windkessel is constructed as a prestretched sleeve of silicone rubber which is enclosed in a larger rigid tube to set a maximum limit on the volume of drug in the windkessel. Typical values are a windkessel volume of 120 micro-liters and pressure of 100 mm Hg, a 1.40 meter capillary of 80 micro-meters inside diameter, and a drug viscosity of 7 cp. This delivers the 120 micro-liters at a substantially constant rate over an 8 hour period. If the pump-chamber is reactuated prematurely, it simply refills the windkessel.

Figure 3:
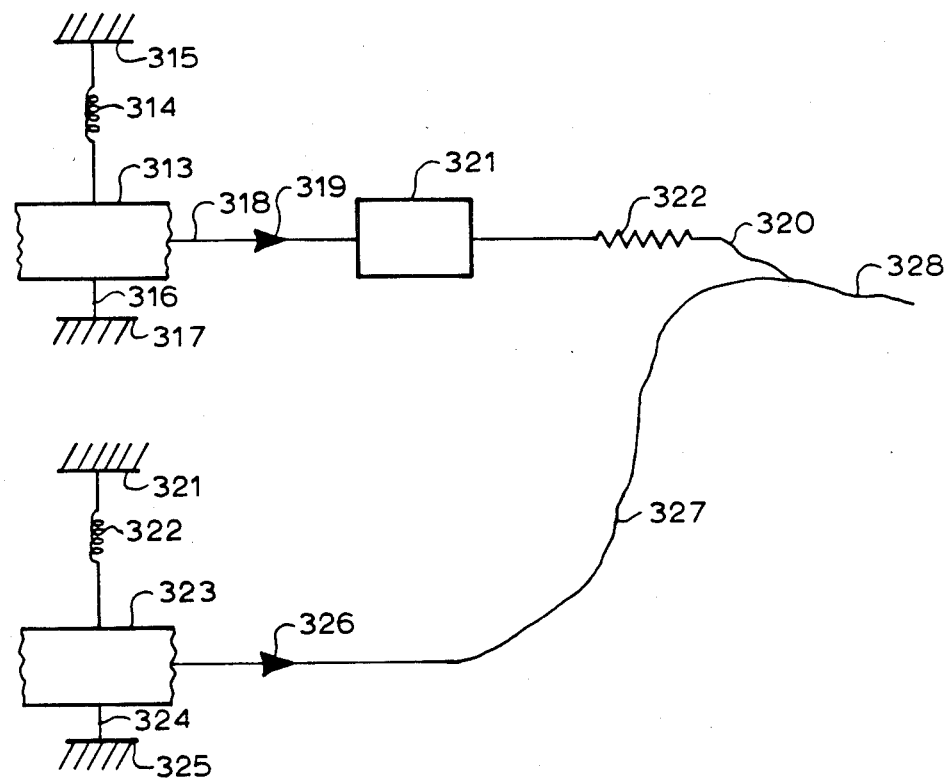
FIG. 3 is a schematic diagram of a second alternative embodiment of the present invention.

Referring next to FIG. 3, a configuration is shown which is particularly suitable for diabetic patients needing insulin. Again, it is to be understood that the equivalent of apparatus of FIG. 1 connected to input of pump chamber 113, is assumed to be connected to each input of pump chambers 313 and 323, thus providing proper fluid or insulin supply from the reservoir to both chambers 313 and 323. This input apparatus including the reservoir is not shown, to enhance clarity of presentation.

Springs 314 and 322 and fixed supports 315, 316/317, 321, 324/325 are equivalent to their earlier described counterparts. Pump chambers 313 and 323 are resilient, and are each operable as earlier described. Fluid output of chamber 313 passes through one way value 319 to windkessel 321, the output of which is conducted to catheter 328. Fluid output of chamber 323 passes through one-way valve 326 and directly thereafter to catheter 328. For diabetics, where a long steady dosage of insulin (via windkessel 321) is desirable, supplemented by as-needed dosages of insulin (from chamber 323) over and above the steady insulin stream, this design is particularly useful. Choice of resistance value, and chamber sizes can control the ratio of "steady flow" or "background" of insulin to "pulsated" or "supplementary" insulin, as may be desired for any particular patient.

Figure 4:
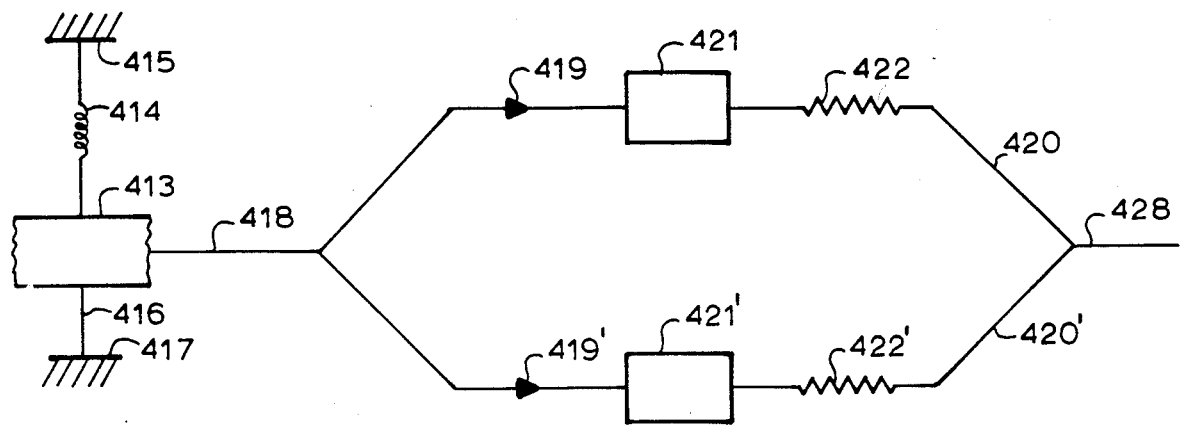
FIG. 4 is a schematic diagram of a third alternative embodiment of the present invention.

Referring to FIG. 4, a dual-rate infusion pump is schematically represented by two windkessels connected from a common chamber, as shown. Again, it is to be understood that the equivalent of apparatus of FIG. 1 connected to input of pump chamber 113, is assumed to be connected to the input of pump chamber 413, thus providing proper fluid supply from the reservoir to chamber 413. The input apparatus is again not shown, to enhance clarity of presentation. Spring 414 and fixed supports 415, 416/417 are equivalent to their earlier described counterparts. Pump chamber 413 is resilient and is operable as earlier described. Fluid output of chamber 413 is directed to windkessel 421 through one way value 419, and to windkessel 421' through one way valve 419'. Output of windkessel 421 is directed through resistance 422 to catheter 428, and output of windkessel 421' is directed through fluid resistance 422' to catheter 428. By judicious selection of resistance values, windkessel volumes and coefficients of elasticity, one can design a system whereby two flow rates into the catheter are achieved. For example, windkessel 421 can provide a 24 hour flow and windkessel 421' can provide a six hour flow on top of the flow from windkessel 421. This dual rate infusion pump has particular application in cancer chemotherapy with anti-neoplastic agents having a significant diurnal variation in activity.

Figure 6:
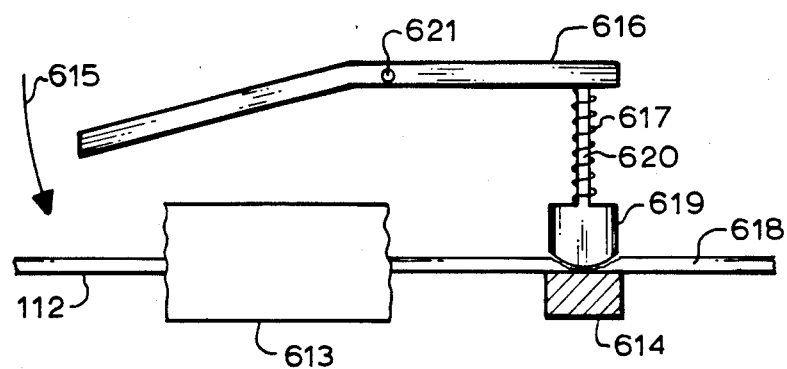
FIG. 6 is a schematic diagram of an alternative embodiment of a one way valve of the present invention.

Referring to FIG. 6, there is shown (schematically) a normally closed clamp, which is an alternative embodiment to one way valve 119 of FIG. 1. Spring 617 normally exerts force on catheter 618 through shaft 620 and clamp head 619 and against fixed support 614, so as to prevent fluid flow from chamber 613 into and through catheter 618. Lever bar 616 is normally supported (pin 621) so as to permit spring 620 to exert the force described, and when bar 616 is displaced in angular direction 615, it causes both spring 617 to relax permitting catheter 618 to open, and presses against chamber 613, forcing fluid into catheter 618. In a particular embodiment the lever bar 616 is actually part of the protective cover over the pump chamber.

In another embodiment of the present invention for providing delay between doses, (not shown in the drawings appended herein), two windkessel/balloon mechanisms (one normally inflated and the other normally deflated) are interconnected by a parallel connection of a resistance path and a one-way valve path, with the easy or open valve flow oriented in a direction away from the normally inflated windkessel balloon (Balloon A) towards the normally deflated windkessel/balloon (Balloon B). Balloon B is arranged to be able to press against the pump chamber when inflated. Thus, in use, pressing on Balloon A would instantly displace the working fluid (a closed hydraulic system) to Balloon B through the open valve parallel path, which would thus indirectly and immediately operate the pump chamber. The working fluid then slowly returns through only the resistance path to Balloon A allowing the pump chamber to refill from the reservoir sac with the desired time delay between doses.

Figure 7:
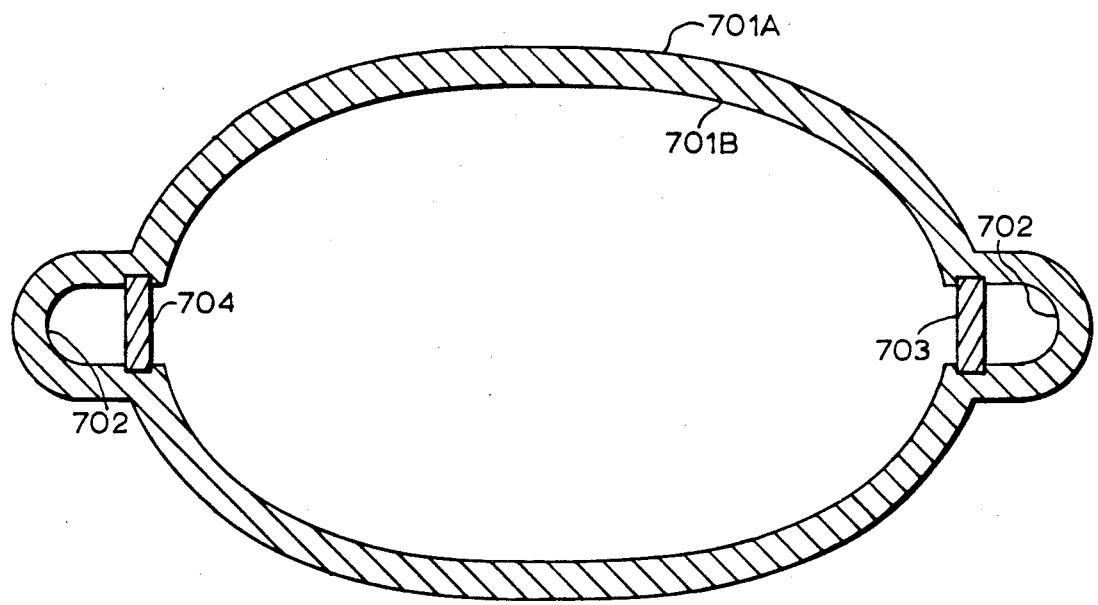
FIG. 7 is a crossection of reservoir sac 106 showing crossections of hydrophilic microporous filters and a crossection of a collecting tube.

Referring to FIG. 7, there is shown a crossection of the wall of reservoir sac 106 depicted in FIG. 1. Outer surface 701A and inner surface 701B of the reservoir sac wall are continuous and form a volume internal to inner surface 701B capable of containing fluid employed in the present invention. Surface 702, although a continuation of inner surface 701B, is also a crossection of the inner surface of a collection tube. The tube (not shown) runs around the periphery of sac 106. Fluid from inside the sac passes into the collection tube through hydrophilic microporous filters 703 and 704, (constructed from a particular type of filter paper in a specific embodiment of the invention) which permit fluid but not air to pass. The collection tube has multiple connections to the fluid in sac 106 through multiple filters which can be spaced at regular intervals around the periphery of the sac. The crossections of only two such filters are shown herein. The tube is connected through bacterial filter 109 (FIG. 1) and resistance 111 (FIG. 1) to pump chamber 113 (FIG. 1). The reason for the hydrophilic microporous filters is to permit the pump to work properly - if filled with air the pump malfunctions. The mechanism prevents reservoir air from flowing into the pump chamber.

The invention may be embodied in yet other specific forms without departing from the spirit or essential characteristics thereof. Thus, the present embodiments are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. Pump apparatus capable of being implanted in the body of a patient, and therein capable of being externally, manually operated by said patient, said apparatus comprising:

reservoir means for holding fluid to be pumped and having a reservoir-outlet to permit egress of said fluid;

pump means, including a pump chamber having a pump chamber inlet and having a pre-formed shape and a pre-determined maximum volume and being hydraulically connected by flow path means from said reservoir-outlet to said pump chamber inlet, for receiving up to said maximum volume of said fluid from said reservoir means, and responsive to application of manual force by said patient for supplying no more that said maximum volume of said fluid through a pump chamber outlet into said flow path means to said patient, said flow path means having a discrete hydraulic resistance device located within said flow means between said reservoir means and said pump chamber for controlling the rate by which said pump chamber reacquires up to said maximum volume of said fluid, said pump means further including catheter means connected to said pump chamber outlet for directing said no more than said maximum volume of said fluid to a particular location within said patient, and, windkessel means for receiving said up to said maximum volume of said fluid from said pump means during a first time interval, and for supplying said up to said maximum volume of said fluid at a relatively constant flow rate to said catheter means during a second time interval longer than said first time interval.

2. The apparatus of claim 1 and wherein said windkessel means includes balloon means for expanding upon receipt of said up to said maximum volume of said fluid, and for contracting upon supplying said up to said maximum volume of said fluid to said catheter means, and fluid resistance means hydraulically connected between output of said balloon means and input of said catheter means for controlling duration of said second time interval.

3. The apparatus of claim 1 and further including a second pump means including a second pump chamber having a second preformed shape and a second pre-determined maximum volume, and being hydraulically connected from said reservoir means, for receiving up to said second pre-determined maximum volume, and responsive to application of a second manual force by said patient for immediately supplying no more than said second maximum volume of said fluid to said catheter.

4. The apparatus of claim 1 and further including additional windkessel means for receiving said up to said maximum volume of said fluid from said pump means during said first time interval, and for supplying said up to said maximum volume of said fluid at a different relatively constant flow rate to said catheter means during a third time interval longer than said first time interval and different from said second time interval.

* * * * *